Dec. 25, 1973 D. E. WORTMAN Re. 27,849
DYNAMIC ACTION VALVELESS ARTIFICIAL HEART
UTILIZING DUAL FLUID OSCILLATOR
Original Filed Nov. 20, 1969
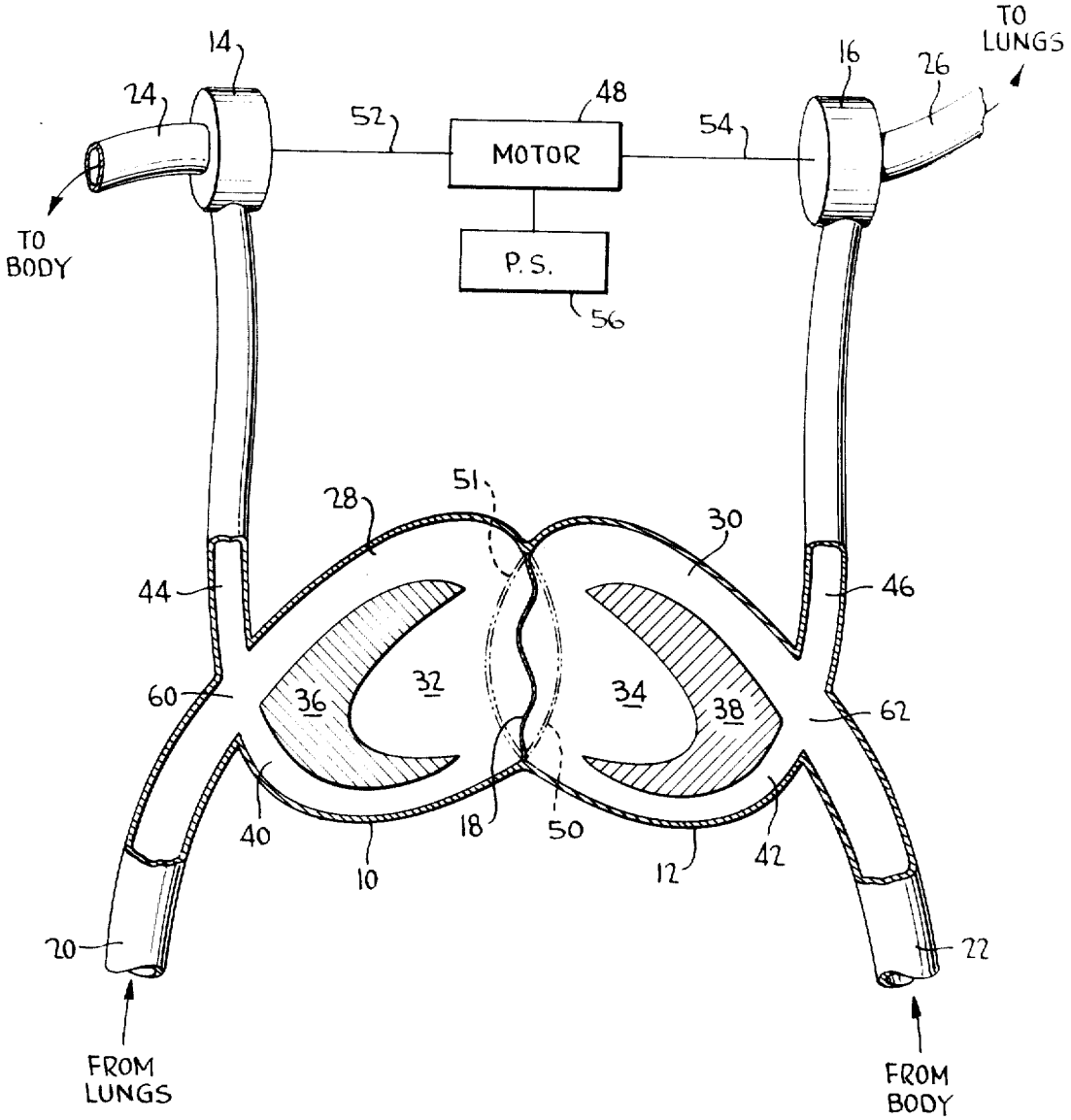
INVENTOR,
DONALD E. WORTMAN
BY Harry M. Saragovitz
Edward J. Kelly
Herbert Berl
J. D. Edgerton
ATTORNEYS United States Patent Office Re. 27,849
Reissued Dec. 25, 1973

27,849

DYNAMIC ACTION VALVELESS ARTIFICIAL HEART UTILIZING DUAL FLUID OSCILLATOR

Donald E. Wortman, 609 Muriel St.,
Rockville, Md. 20852

Original No. 3,599,244, dated Aug. 17, 1971, Ser. No. 878,484, Nov. 20, 1969. Application for reissue Nov. 30, 1971, Ser. No. 203,489
Int. Cl. A61f *1/24*
U.S. Cl. 3—1 12 Claims

Matter enclosed in heavy brackets [ ] appears in the original patent but forms no part of this reissue specification; matter printed in italics indicates the additions made by reissue.

ABSTRACT OF THE DISCLOSURE

An artificial heart intended for supplementing or [temporarily] replacing the natural heart for circulating blood through the body. The heart relies on the dynamic flow properties of the blood for its operation, utilizing a unique dual fluid oscillator with a common diaphragm for providing the pulsing action to a pair of pumps that have pressure-volume flow relationships that simulate the natural heart.

RIGHTS OF GOVERNMENT

The invention described herein may be manufactured, used, and licensed by or for the United States Government for governmental purposes without the payment to me of any royalty thereon.

BACKGROUND OF THE INVENTION

The present invention relates generally to an artificial heart and more particularly to an electromechanical system that incorporates the principles of fluidics to provide a device for use as a [temporary] *total* replacement for or as an aid to the heart in circulating blood throughout the body.

Devices heretofore developed and intended for use as artificial hearts have fallen far short of their expectations, one reason being their inherent complexity. Earlier embodiments of artificial hearts while attempting to simulate as closely as possible the action of the human heart, were dependent for their operation upon a multitude of moving parts such as valves, flexible chambers, and displacement-type pumps, plus sophisticated synchronous control systems and sensors for either speeding up or slowing down the pumping action or "heartbeat." Such devices have been found to require relatively large power supplies and to occupy large volumes in addition to being prohibitively expensive, thus detracting from their usefulness as *a total replacement organ* [an aid to the natural heart]. Additionally, such devices have not been suited for prolonged service: valves tend to wear out, leak, lose their efficiency and promote blood clots; pumps and collapsible chambers tend to exert large compressive forces upon the blood to the point where the blood would become damaged; and many other moving parts wear out or become inefficient.

It is therefore an object of the present invention to provide an artificial heart that is capable of [temporarily] replacing or aiding the natural heart by completely or partially taking over the operation of pumping blood through the circulatory system.

It is another object of the present invention to provide an artificial heart that is inherently pressure sensitive and thus does not require any external regulating mechanism for long term use.

It is an additional object of the present invention to provide an artificial heart which will be chemically inert and which will not destroy or be destroyed by the blood which it pumps.

A further object of the present invention is to provide a greatly simplified artificial heart that simulates the action of the natural heart to a high degree and yet is valveless and contains no collapsible chambers.

A still further object of the present invention is to provide an artificial heart that is economical to manufacture, has very few moving parts, and does not damage the blood in operation.

SUMMARY OF THE INVENTION

Briefly, in accordance with this invention, an artificial heart is provided for use as either a *total replacement* [supplement to] for the natural heart to be implanted in the chest of the user or as an external *supplement* [temporary replacement] during surgery or the like. The device of the present invention is characterized by two interdependent fluid oscillators and two free-running fluid pumps. The oscillators are separated by a common flexible diaphragm which allows alternate pulsing to the two pumps. The pumps are run continuously at a preselected speed and have pressure-volume flow response which simulate the natural heart. The present invention provides great improveemnt over prior art in that it simulates the action of the natural heart and yet has no valves to clog the blood and no collapsible chambers to squeeze or crush the blood thus minimizing deterioration and wear of the device itself while allowing more efficient and dependable operation.

BRIEF DESCRIPTION OF THE DRAWING

The specific nature of the invention as well as other objects, aspects, uses, and advantages thereof will clearly appear from the following description and from the accompanying drawing, in which:

The drawing is a schematic partial cross section illustration of an artificial heart in accordance with the present invention.

DESCRIPTION OF THE PREFERRED EMBODIMENT

A brief review of the natural heart's pumping action will facilitate understanding of the efficiency with which the present invention simulates the actions of the natural heart.

The heart is a muscular organ divided into four chambers. The upper chamber on each side of the heart is called an auricle and below each auricle is another chamber called the ventricle. Deoxygenated blood from the body enters the right auricle of the heart through two large veins. The blood-filled right auricle then contracts, sending the blood into the right ventricle through the tricuspid valve. The right ventricle then contracts, which simultaneously closes the tricuspid valve and opens the semilunar valve leading to the lungs via the pulmonary artery. From the lungs, oxygen-enriched blood flows into the left auricle through the pulmonary vein. The filled left auricle contracts, forcing blood through the mitral valve into the left ventricle which in turn will contract and force the blood through another semilunar valve into the aorta which is the main artery to the body.

It is evident that an artificial heart built to the above specifications to operate over an extended period of time would encounter many mechanical difficulties due to inevitable deteriorations of its numerous valves, chambers and contraction apparatus. The present invention, while efficiently [aiding] *producing* the final result of the natural heart, does not attempt to duplicate its actions. Rather it employs well-known fluidic principles in a unique dual fluid oscillator that provides alternate pulsing to a pair of fluid pumps that respond to pressure input variations as would the natural heart.

The drawing illustrates the artificial heart of the present invention, showing a cross-sectional view of a preferred embodiment of the dual fluidic oscillator and a schematic representation of the pumps and associated hardware. The dual fluidic oscillator is comprised of two back-to-back RCR (resistance-capacitance-resistance) fluid oscillators shown at 10 and 12 and internally separated by a flexible diaphragm 18 which is made of a suitable nonporous material such as silicone rubber. The two oscillators 10 and 12 provide a pulsed flow of blood to two fluid pumps 14 and 16 by way of the conduits 44 and 46, respectively. The input to oscillators 10 and 12 is received from conduits 20 and 22, respectively, and proceeds to travel the RCR flow paths in each oscillator as defined by resistance conduits 28 and 30, capacitance tanks 32 and 34 and resistance conduits 40 and 42, before exiting to pumps 14 and 16 by way of conduits 44 and 46, respectively. The oscillators 10 and 12 alternately oscillate at a frequency that varies directly as the flow of blood through the body varies. When the body is at rest, there exists a low blood flow and the frequency of oscillation will automatically lower. When the body is at work and more blood flows in the system, the oscillation will increase in frequency to pump more blood. In other words, the operation of the system is based on the dynamic properties of blood flow. The back-to-back fluid oscillators 10 and 12 each operate much like a standard RCR fluid oscillator but for the addition of the flexible diaphragm 18 which separates capacitance chambers 32 and 34 and allows the device a certain compliance with blood pressure variations and provides the pulsing action of the artificial heart.

Pumps 14 and 16 have the characteristics that their outputs are directly related to their input pressure and inversely related to the pressure head against which they are pumping. The pumps thus respond to pressure variations at their inlets 44 and 46 and outlets 24 and 26 in a fashion analogous to the natural heart. One embodiment of a pump possessing such characteristics that could be utilized in the present invention is known in the art as a centrifugal pump. Centrifugal pumps have been shown to pump blood in a highly efficient and non-destructive manner, as evidenced by the F. Dorman et al. paper in Vol. XV of The Transactions of the American Society of Artificial Internal Organs 1969, entitled "Progress in the Design of a Centrifugal Cardiac Assist Pump with Trans-cutaneous Energy Transmission by Magnetic Coupling." Pumps 14 and 16 are powered by a motor 48 which drives shafts 52 and 54, and a power supply 56. Much effort has been directed towards perfecting implantable motors and power supplies for the uses described herein, whereas external equivalents are also well known in the art. The entire heart can be constructed of a material that is noncorrosive, has nonoccluding surfaces, and does not damage the blood in any way.

In operation, consider the deoxygenated blood to be entering the artificial heart from the body through conduit 22 to fill a nearly empty capacitance tank 34 through resistance conduit 30. The near-emptiness of capacitance tank 34 implies that capacitance tank 32 of oscillator 10 is nearly full and diaphragm 18 is in position 50. As tank 34 becomes filled with blood, diaphragm 18 moves from position 50 towards position 51. The increased pressure on diaphragm 18 from the blood in tank 34 will force the oxygen-rich blood in nearly full tank 32 to exit through resistance conduit 40 which acts as a control jet for blood subsequently entering conduit 20 from the lungs. The control jet issuing from conduit 40 will impinge upon the blood entering interaction region 60 and divert it to conduit 44 which leads to pump 14 which pumps the oxygen-rich blood out conduit 24 to the body. This action continues until tank 32 is nearly empty and diaphragm 18 is fully in position 51, which would imply a nearly full supply of deoxygenated blood in tank 34. Once the diaphragm is in position 51, no force is exerted on the blood remaining in tank 32 and thus the control jet will cease to issue from conduit 40. Part of the blood entering along conduit 20 will then reattach to resistance conduit 28 and begin to fill tank 32 once more. As tank 32 fills with blood, diaphragm 18 will move towards position 50 and exert pressure on the blood nearly filled tank 34 forcing the blood to exit through resistance conduit 42 which now acts as a control jet to impinge upon the main stream of blood entering conduit 22 from the body. The main stream entering conduit 22 is thus deflected and attaches to conduit 46 which leads to pump 16, which pumps the deoxygenated blood out conduit 26 to the lungs. Once the blood has been nearly emptied from tank 34 and diaphragm 18 is in position 50, the control jet from conduit 42 will slow to a trickle and eventually cease. Part of the blood subsequently entering conduit 22 will reattach along conduit 30 and the above cycle will repeat itself. The foregoing description encompasses one cycle in the operation of the artificial heart; i.e. one pulse has issued from each oscillator to each pump. The duration of a single cycle is controlled in part by the dimensions of the resistance conduits and the capacitance tanks which can be varied for each patient's needs by the positioning of the partitions 36 and 38.

During the alternate pulsing of oscillators 10 and 12, pumps 14 and 16 are running continuously and at the same speed. The pumps will pump only that blood that is present at their inlets. Thus if the blood pressure increases or decreases and forces the frequency of oscillation to do likewise, the pumps would automatically adjust to the change in pulsatile flow.

From the foregoing it is apparent that I have provided a greatly improved artificial heart capable of [assisting the natural heart by] complete implantation within the body or for use as an external [temporary] aid to circulation. The device heretofore described is simple and uncomplicated, relying on the dynamic flow properties of the blood for its operation. No valves or collapsible chambers are used, which makes the device less susceptible to wear and tear while insuring further that the blood remains undamaged. The entire apparatus can be constructed with a material that is noncorrosive and easily adaptable to the use intended.

I wish to be understood that I do not desire to be limited to the exact details of construction shown and described, for obvious modifications will occur to a person skilled in the art. For example, the positions of the pumps and oscillators could be interchanged if greater complicance with the circulating system could be attained.

I claim as my invention:

1. An artificial heart to act as a [circulatory aid] *substitute* for the natural heart either internally or externally of the body comprising (a) first and second pulsing means for producing first and second pulsed flows of blood, respectively, each of said pulsing means comprising (1) an input conduit for receiving a mainstream of blood, (2) a capacitance chamber to store said mainstream of blood until a certain volume is attained, (3) a control conduit for transmitting the blood from said capacitance chamber to deflect said mainstream of blood upon the application of forcing means, said forcing means comprising a flexible diaphragm located between and physically separating said capacitance chambers whereby blood is ejected from one of said capacitance chambers by a force on the diaphragm applied by the blood that is filling the other of the said capacitance chambers, said filling and ejecting being a continuous alternating action whose repetition frequency is dependent upon the rate of flow of blood through the system, and (4) an output conduit for receiving said mainstream of blood after its deflection by the blood issuing from said control conduit, (b) first and second pumping means for receiving and pumping said first and second pulsed flows of blood to the remainder of the circulatory system, the output volume flow of said first and second pumping means being directly proportional to the input pressure of the said first and second pulsed flows of blood and inversely proportional to the pressure against which they are pumping; and (c) power means to drive said first and second pumping means at a continuous and nonvarying speed.

2. The artificial heart of claim 1 wherein said first and second pumping means each are comprised of a centrifugal pump.

3. The invention according to claim 1 wherein said first and second pumping means are located at the inlets of said first and second pulsing means.

*4. An artificial heart for supplementing or replacing a natural heart for circulating blood through a body, comprising:*

*(a) first means for pumping oxygenated blood from the lungs of said body to the remainder of the circulatory system of said body;*

*(b) second means for pumping deoxygenated blood from said remainder of said circulatory system to said lungs;*

*(c) a first fluid oscillator adapted to receive oxygenated blood from said lungs and emit said oxygenated blood in a pulse fashion to said remainder of said circulatory system; and*

*(d) a second fluid oscillator adapted to receive deoxygenated blood from said remainder of said circulatory system and emit said deoxygenated blood in a pulsed fashion to said lung;*

*(e) said first pumping means connected in series with said first fluid oscillator and said second pumping means connected in series with said second fluid oscillator.*

*5. The artificial heart of claim 4 wherein said first fluid oscillator is located at the inlet of said first pumping means.*

*6. The artificial heart of claim 4 wherein said second fluid oscillator is located at the inlet of said second pumping means.*

*7. The artificial heart of claim 4 wherein said first fluid oscillator is located at the outlet of said first pumping means.*

*8. The artificial heart of claim 4 wherein said second fluid oscillator is located at the outlet of said second pumping means.*

*9. The artificial heart of claim 4 wherein said first and second pumping means each have the characteristic that the output flow therefrom is directly related to the input pressure and inversely related to the output pressure.*

*10. The artificial heart of claim 4 wherein said first and second pumping means each comprise a centrifugal pump.*

*11. The artificial heart of claim 4 wherein each of said fluid oscillators comprises:*

*(a) an input conduit for receiving a mainsteam of blood;*

*(b) a capacitance chamber to store the blood received from said input conduit until a certain volume therein is attained;*

*(c) a control conduit for transmitting the blood from said capacitance chamber to deflect said mainstream of blood; and*

*(d) an output conduit for receiving said mainstream of blood after its deflection by the blood issuing from said control conduit;*

*(e) said mainstream of bood re-entering said input conduit upon the cessation of flow of blood through said control conduit.*

*12. The artificial heart of claim 11 wherein each of said fluid oscillators further comprises a flexible diaphragm adjacent to said capacitance chamber, said diaphragm expanding as blood fills said capacitance chamber, said diaphragm contracting upon the attainment of said certain volume of blood in said capacitance chamber to help force blood through said control conduit, said expanding and contracting of said diaphragm tending to create a pulsed output of blood.*

References Cited

The following references, cited by the Examiner, are of record in the patented file of this patent or the original patent.

UNITED STATES PATENTS

| | | | |
|---|---|---|---|
| 3,148,624 | 9/1964 | Baldwin | 3—DIG. 2 |
| 3,208,448 | 9/1965 | Woodward | 128—1 R |
| 3,487,784 | 1/1970 | Rafferty et al. | 128—1 R X |

OTHER REFERENCES

"An Ideal Heart Pump With Hydrodynamic Charateristics Analogous to the Mammalian Heart," by G. A. Saxon et al., Trans. Amer. Soc. Artif. Int. Organs, vol. VI, 1960, pp. 288–291.

"Progress in the Design of a Centrifugal Cardiac Assist Pump With Trans-cutaneous Energy Transmission by Magnetic Coupling," by F. Dorman et al., Trans. Amer Soc. Artif. Int. Organs, vol. XV, 1969, pp. 441–448.

RICHARD A. GAUDET, Primary Examiner

R. L. FRINKS, Assistant Examiner

U.S. Cl. X.R.

3—DIG. 2; 128—1 R, DIG. 10; 137—81.5; 417—350